United States Patent
Fresquet et al.

(10) Patent No.: US 10,043,266 B2
(45) Date of Patent: Aug. 7, 2018

(54) METHOD AND DEVICE FOR CONTROLLABLY REVEALING STRUCTURES BURIED IN OBJECTS SUCH AS WAFERS

(71) Applicant: FOGALE NANOTECH, Nimes (FR)

(72) Inventors: Gilles Fresquet, Garrigues Sainte Eulalie (FR); Sylvain Perrot, Palaiseau (FR)

(73) Assignee: UNITY SEMICONDUCTOR, Montbonnot-Saint-Martin (FR)

( * ) Notice: Subject to any disclaimer, the term of this patent is extended or adjusted under 35 U.S.C. 154(b) by 327 days.

(21) Appl. No.: 14/422,300

(22) PCT Filed: Aug. 20, 2013

(86) PCT No.: PCT/EP2013/067339
§ 371 (c)(1),
(2) Date: Feb. 18, 2015

(87) PCT Pub. No.: WO2014/029784
PCT Pub. Date: Feb. 27, 2014

(65) Prior Publication Data
US 2015/0228069 A1    Aug. 13, 2015

(30) Foreign Application Priority Data

Aug. 21, 2012  (FR) ..................... 12 57906
Mar. 12, 2013  (FR) ..................... 13 52172

(51) Int. Cl.
*H04N 9/47*   (2006.01)
*H04N 7/18*   (2006.01)
(Continued)

(52) U.S. Cl.
CPC .......... *G06T 7/0012* (2013.01); *B24B 37/005* (2013.01); *B24B 49/12* (2013.01);
(Continued)

(58) Field of Classification Search
None
See application file for complete search history.

(56) References Cited

U.S. PATENT DOCUMENTS 5,821,549 A    10/1998  Talbot
7,738,113 B1   6/2010   Marx et al.
(Continued)

OTHER PUBLICATIONS

S. Perrot et al., "A Versatile Optical System for Metrology and Defects Inspection of 3D Integration Processes", LTB-3D, Tokyo, May 22-23, 2012, p. 191.

*Primary Examiner* — Chikaodili E Anyikire
(74) *Attorney, Agent, or Firm* — Greer, Burns & Crain, Ltd.

(57) ABSTRACT

An imaging method and device is provided for inspecting for the presence, in an object like a wafer, of enclosed structures, such as vias, employing: an imaging sensor; an optical imager able to produce, on the imaging sensor, an object image in a field of view; and an illuminator for generating an illuminating beam and lighting the field of view in reflection, including: acquiring a first image of the object by illuminating the object with a first illuminating beam adapted to the object, such that the light of the beam penetrates the object; acquiring a second image of the object by illuminating the object with a second illuminating beam adapted to the object, such that the light of the beam is reflected by the surface of the object; and comparing the first and second images to identify structures that appear in the first image but not in the second image.

12 Claims, 3 Drawing Sheets

(51) Int. Cl.
  *G06T 7/00* (2017.01)
  *B24B 49/12* (2006.01)
  *G01B 11/06* (2006.01)
  *G01N 21/95* (2006.01)
  *B24B 37/005* (2012.01)
  *G01B 9/02* (2006.01)
  *G01B 11/14* (2006.01)
  *H04N 5/225* (2006.01)

(52) U.S. Cl.
  CPC .......... *G01B 9/02091* (2013.01); *G01B 11/06* (2013.01); *G01B 11/0633* (2013.01); *G01B 11/0683* (2013.01); *G01B 11/14* (2013.01); *G01N 21/9501* (2013.01); *G06T 7/001* (2013.01); *G06T 7/0008* (2013.01); *H04N 5/2256* (2013.01); *H04N 7/18* (2013.01); *G06T 2207/10004* (2013.01); *G06T 2207/10152* (2013.01); *G06T 2207/30148* (2013.01)

(56) References Cited

U.S. PATENT DOCUMENTS

| | | | |
|---|---|---|---|
| 2006/0192953 A1* | 8/2006 | Fukazawa | G01B 11/30 356/237.5 |
| 2007/0081151 A1 | 4/2007 | Shortt et al. | |
| 2007/0181151 A1* | 8/2007 | Guthrie | C23G 1/26 134/6 |
| 2012/0019707 A1 | 1/2012 | La Lumondiere et al. | |
| 2012/0122252 A1* | 5/2012 | Fujimori | G01N 21/95692 438/16 |
| 2013/0038863 A1 | 2/2013 | Fresquet | |

* cited by examiner

METHOD AND DEVICE FOR CONTROLLABLY REVEALING STRUCTURES BURIED IN OBJECTS SUCH AS WAFERS

BACKGROUND

The present invention relates to a device and method for making dimensional measurements on multi-layer objects such as wafers. It also relates to an imaging device making it possible to locate structures below the surface of such objects, in particular for the purpose of positioning measuring sensors relative to these structures.

The present invention also relates to a method and an imaging device for controllably revealing structures buried in objects such as wafers.

The field of the invention is more particularly but not limitatively that of the measurement and dimensional control of devices in the field of microelectronics, microsystems (MEMs) or integrated optics.

Manufacturing techniques for microelectronics and microsystems (MEMs, MOEMs) are developing towards the production of complex volume structures, which can allow better integration of the functions of these systems in their volume.

These structures are characterized by the superimposition of a number, sometimes a large number, of layers of components, with interconnection tracks (or vias) which connect these layers of components. These techniques belong to what is frequently called "chip level packaging" or "3D integration".

The layers of components can be produced on separate wafers, which are then superimposed and interconnected.

More precisely, the manufacturing methods can comprise the following steps:
  etching of the vias, which are present as holes or trenches opening on only one side of the wafer (the components surface);
  metallization of the vias and at least partial production of the conductor tracks and components on the components surface,
  thinning of the wafer by polishing (usually by a mechanical method) of the rear surface (i.e. the surface opposite the components surface). The wafer is stuck to a temporary transport wafer in order to obtain sufficient mechanical rigidity. In fact, after polishing, the thickness of the wafer can be reduced to a few tens of micrometres.

The thinning makes it possible to reduce the thickness of the wafer to a predetermined thickness, or until the vias break through.

It is very important to control the thickness of residual material between the bottom of the vias and the rear surface of the wafer during the thinning operation.

Different techniques are known which make it possible to measure this thickness of residual material.

For example, techniques based on time-domain or spectral-domain low-coherence interferometry are known.

The document U.S. Pat. No. 7,738,113 by Marx et al. is also known, which describes a device making it possible to carry out this measurement with probes based on a scanning confocal technique or chromatic dispersion confocal technique.

However, the problem arises of locating the vias which cannot be seen from the rear surface of the wafer. This problem is not trivial as these vias may be a few micrometres or a few tens of micrometres wide, and it must be possible to accurately position in line with them a measurement beam the diameter of which is not much greater.

It is known to couple point distance-measuring sensors with an imaging system which produces an image of the surface of the wafer, and which makes it possible to accurately position the measurement beams.

These systems do not make it possible to solve this problem of positioning because:
  as explained previously, the vias cannot be seen from the rear surface of the wafer;
  at the time when the thinning operation is carried out, there are already components and metal tracks which can take up several square millimetres on the components surface of the wafer. These components completely mask the position of the vias, and they are moreover completely opaque, which prevents location of the vias by transparency.

Beyond this particular problem, the development of the "chip level packaging" techniques results in a need to be able to accurately measure thicknesses or positions of multiple layers of stacked materials.

These layers can be of the order of a micrometre or less up to several hundred micrometres, and there may be a large number of them. In practice, none of the measuring methods previously mentioned (interferometry or confocal) is capable of satisfying all of the specifications for this type of measurement, which in practice leads to having to multiply the measurement devices.

During a wafer thinning operation, it is sometimes also very important to check whether vias have broken through, i.e. whether they are apparent on the polished or thinned surface. This makes it possible in particular to optimize the thinning operation and to stop it when all the vias are "revealed", i.e. when they appear on the thinned surface.

An object of the present invention is to overcome the drawbacks of the prior art relating to distance and thickness measurements on complex structures.

An object of the present invention is in particular to propose a system which makes it possible to locate vias or similar structures which cannot be seen from the surfaces of a wafer.

An object of the present invention is also to propose a system which makes it possible to carry out residual thickness measurements on vias from the rear surface of a wafer.

Finally, an object of the present invention is to propose a system which makes it possible to carry out thickness measurements in an extensive dynamic range and on a high number of interfaces.

An object of the present invention is also to propose a method and an imaging device making it possible to check, during polishing, whether vias have become apparent.

SUMMARY

This objective is achieved with a method for controlling for the presence, at a surface of an object such as a wafer, of structures enclosed in said object, such as vias, utilizing an imaging sensor,
optical imaging means capable of producing, on said imaging sensor, an image of the object in a field of view, and illuminating means for generating an illuminating beam and lighting said field of view in reflection, characterized in that it comprises steps of:
  acquiring a first image of the object by illuminating said object with a first illuminating beam the spectral content of which is suited to the nature of the object, so that the light of said beam is capable essentially of penetrating into said object, acquiring a second image of the object by illuminating said object with a second illuminating beam the spectral content of which is suited to the nature of the object so that the light of said beam is essentially reflected by the surface of the object, and comparing said first and second images so as to identify structures that appear in the first image but not in the second image.

According to another aspect, an imaging device is proposed for controlling for the presence, at a surface of an object such as a wafer, of structures such as vias enclosed in said object (and/or for locating structures through the surface of an object such as a wafer, in particular with a view to positioning a measuring sensor relative to said structures), comprising:

an imaging sensor, optical imaging means capable of producing, on said imaging sensor, an image of the object in a field of view, illuminating means for generating an illuminating beam and lighting said field of view in reflection, in which the illuminating means are capable of generating an illuminating beam the spectral content of which is suited to the nature of the object, so that the light of said beam is capable essentially of penetrating into said object.

The illuminating means can also be capable of generating an illuminating beam the spectral content of which is suited to the nature of the object, so that the light of said beam is essentially reflected by the surface of the object.

According to embodiments, the illuminating means can comprise a spectral filter capable of limiting the spectrum of the illuminating beam to wavelengths which are capable essentially of penetrating into the object.

The spectral filter can comprise:

a plate made of a material identical or similar to a material of the object;

a silicon plate;

a plate filtering the optical spectrum so as to allow only the wavelengths greater than a cutoff wavelength to pass through;

a plate filtering the optical spectrum so as to allow only the wavelengths greater than one micrometre to pass through;

a plate of the high-pass (wavelength) interference filter type. The illuminating means can also comprise:

a light source capable of emitting light with a spectrum comprising first wavelengths capable essentially of being reflected by the surface of the object and second wavelengths capable essentially of penetrating into the object, and switching means for inserting the spectral filter into, or withdrawing it from, the illuminating beam.

According to other embodiments, the illuminating means comprise a light source capable of emitting a light the spectrum of which is limited to wavelengths capable essentially of penetrating into the object.

The illuminating means can also comprise a second light source capable of emitting a light the spectrum of which is limited to wavelengths capable essentially of being reflected by the surface of the object.

According to embodiments, the device according to the invention comprises:

an illuminating beam incident in the field of view along an axis of illumination substantially parallel to the optical axis of the imaging system;

an illuminating beam incident in the field of view along an axis of illumination forming, with the optical axis of the imaging system, an angle greater than the angle defining the numerical aperture of said imaging system.

According to embodiments, the device according to the invention can also comprise a source of light in transmission arranged so as to illuminate the field of view in transmission, through the object.

The imaging sensor can comprise a CCD- or CMOS-type sensor on a silicon substrate.

According to another aspect of the invention, a system is proposed for carrying out dimensional measurements on an object such as a wafer, comprising at least one optical sensor for measuring thickness and/or distance, and an imaging device according to the invention.

The system according to the invention can also comprise:

at least one optical sensor for measuring thickness and/or distance based on a principle of time-domain low-coherence interferometry;

at least one optical sensor for measuring thickness and/or distance based on a principle of spectral-domain low-coherence interferometry, or optical frequency scanning interferometry;

at least one optical sensor for measuring thickness and/or distance with a measurement beam passing through the distal objective of the optical imaging means;

at least one optical sensor for measuring thickness and/or distance, of the chromatic confocal type.

According to embodiments, the system according to the invention can comprise at least two optical sensors for measuring thickness and/or distance, arranged respectively, one on a surface of the object on the side of the optical imaging means and the other on a surface opposite said object.

According to yet another aspect of the invention, a method is proposed for measuring the residual thickness of material between a surface of a wafer and structures such as vias, comprising steps of:

locating said structures through said surface of the wafer by means of an imaging device according to the invention, positioning an optical sensor for measuring thickness and/or distance opposite said structure, and measuring the residual thickness of material.

BRIEF DESCRIPTION OF THE DRAWINGS

Other advantages and features of the invention will become apparent on reading the detailed description of implementations and embodiments that are in no way limitative, and from the following attached drawings.

DETAILED DESCRIPTION

Figure 1:
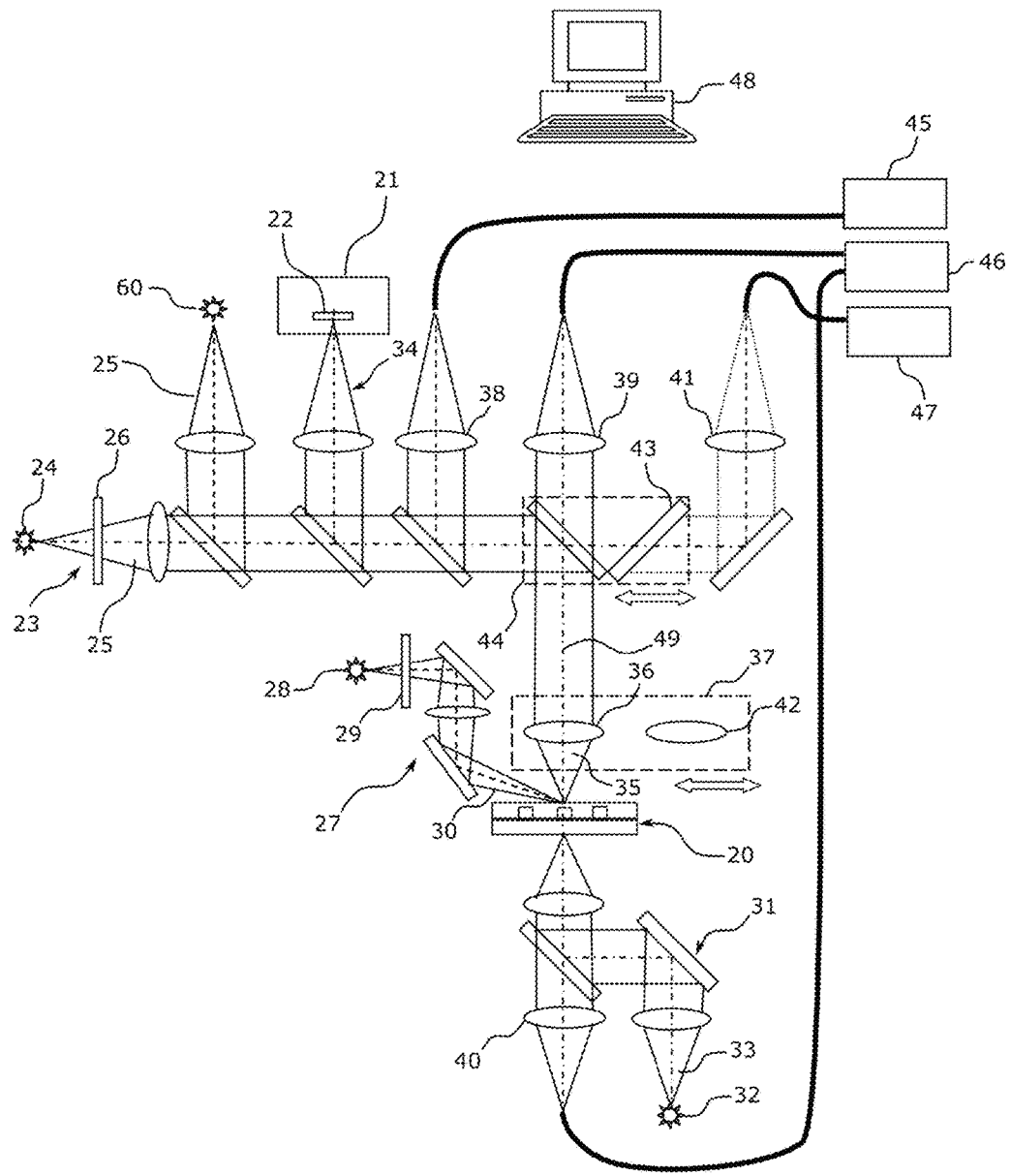
FIG. 1 shows an embodiment of a measurement system according to the invention.

With reference to FIG. 1, the measurement system according to the invention makes it possible to carry out dimensional measurements, including thickness measurements, on a measurement object 20.

Figure 2:
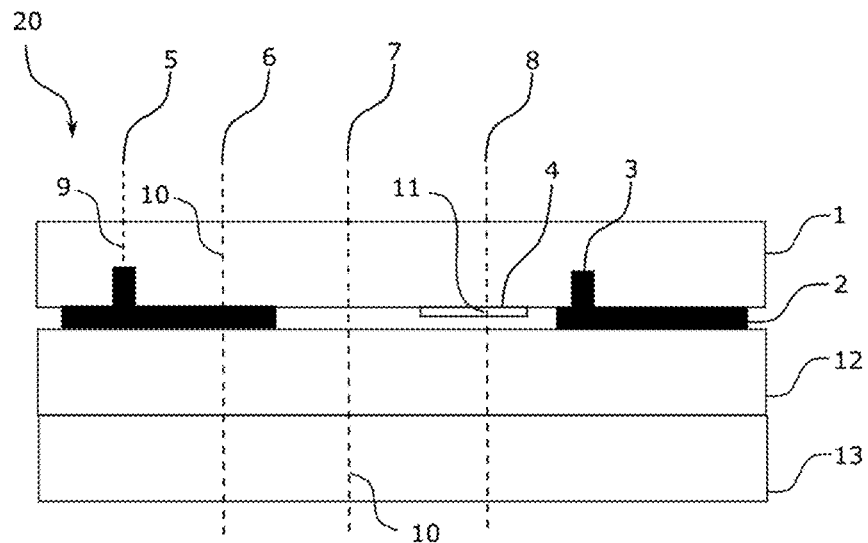
FIG. 2 shows examples of measurement problems solved by the measurement system of FIG. 1.

FIG. 2 shows an example of a measurement object 20 which is constituted by an assembly of layers of materials 1, 12, 13 with components and tracks 2 present on certain interfaces.

This example is purely illustrative and does not aim to faithfully represent a particular step in a process for manufacturing components. It simply shows, in a non-limitative manner, a set of measurement problems which may be encountered, not necessarily simultaneously, during a process for manufacturing components in micro-optics, microsystems or microelectronics, and more particularly when techniques for assembling components in 3 dimensions, or techniques of the "chip level packaging" type are implemented.

It is understood that the measurement system according to the invention can be implemented on measurement objects 20 with any type of materials compatible with the measurement techniques and wavelengths used, subject to routine adaptations within the scope of a person skilled in the art.

These materials can comprise in particular silicon (Si), III-V compounds such as gallium arsenide (GaAs) or indium phosphide (InP), silicon carbide (SiC), sapphire crystal, silica, silicon-on-insulator (SOI) etc. in the form of wafers (flat discs of material), deposited layers etc.

The measurement object 20 shown in the example of FIG. 2 comprises a silicon wafer 1, in which vias 3 have been etched. These vias 3 (or "Through Silicon Vias", TSV) correspond to hollow structures, such as trenches or holes, a few micrometres to several tens of micrometres wide.

The vias 3 are for example intended to produce interconnections between components or metal tracks 2 and other components added, in a subsequent step of the process, to the outer surface of the wafer 1. In this case they are metallized.

To be able to produce these interconnections, it is necessary to thin the wafer 1 to make the vias 3 apparent on its outer surface. This thinning operation is usually carried out by polishing the outer surface of the wafer 1. It requires regular and accurate control of the residual thickness 9 between the vias and the outer surface of the wafer 1 during the process. This measurement is termed an RST ("Remaining Silicon Thickness") measurement.

To be able to carry out this measurement, it must be possible to locate the vias 3 through the surface of the wafer 1 and accurately position the measurement beam of a distance or thickness sensor on the measurement axis 5. Moreover, the vias 3 cannot be located by transparency because they are in line with opaque components 2 with much larger dimensions.

As shown in FIG. 2, other measurement problems are advantageously solved with the system according to the invention:

along the measurement axis 6, measurement of the thickness 10 of stacked structures (or location of the interfaces) when opaque components 2 are situated in the path of the measurement beams;

along the measurement axis 7, measurement of the thicknesses 10 of a large number of successive layers, with location of the interfaces, along the measurement axis 8, thickness measurements in a large dynamic range, on layers of material 11 of the order of a micrometre up to thicknesses of material 10 of several hundred micrometres, with location of the interfaces.

The measurement system of FIG. 1 and the way in which it makes it possible to carry out the measurements of FIG. 2 will now be described.

The measurement system according to the invention comprises:

point optical distance or thickness measuring sensors, which make it possible to acquire measurements along measurement axes 5, 6, 7, 8, an imaging device for visualizing the object 20 and for being able to position the measuring sensors relative to this object, a sample support intended to receive the measurement object 20, with a mechanical positioning system for moving it relative to the imaging device and the measuring sensors.

Imaging Device

The imaging device comprises a camera 21, with an array sensor 22 of the CCD or CMOS type.

A set of optical imaging means 34, essentially constituted by lenses and beam-splitting or beam-combining elements (beam splitters, partially transparent mirrors, cubes), makes it possible to image the object 20 in a field of view on the sensor 22 of the camera 21.

These optical imaging means 34 comprise in particular a distal optic 36, which makes it possible to adjust the magnification of the image. This distal optic comprises a microscope objective mounted on a revolving nosepiece 37 so that it can be easily changed.

The imaging device also comprises illuminating means for lighting the field of view on the object 20.

The imaging device must make it possible to:

visualize the surface of the object 20, in order to make it possible to control it or in order to locate measuring sensors relative to structures which may be present there, locate structures such as components 2, buried in the object 20, in cases where they can be seen by transparency, for example in order to carry out measurements between these structures 2 along the measurement axis 7 of the example of FIG. 2, and also to locate structures such as vias 3, buried in the object 20, in cases where they cannot be seen by transparency, for example in order to carry out measurements on these structures 3 along the measurement axis 5 of the example of FIG. 2.

Moreover, it may be useful to be able to detect both the components 2 and the vias 3, for example to identify the vias 3 relative to the components 2.

The need to be able to visualize both the surface of the object 20 and buried structures 3 which cannot be seen in transparency leads to contradictory constraints: It must be possible in one case to image the surface under good conditions and in the other case to image structures 3 which are sometimes just a few micrometres deep below this surface, without being disturbed by the reflections from the surface.

These problems are solved in the invention thanks to the lighting configurations utilized.

Silicon is a material which is opaque in the visible part of the optical spectrum, and which becomes transparent for wavelengths in the near-infrared, greater than 1 micrometre.

Interestingly, there are cameras 21 based on CCD or CMOS sensors 22 on a silicon substrate which have a sensitivity extending up to wavelengths of 1.1 µm. These cameras have the advantage, over infrared cameras, of remaining standard industrial cameras of moderate cost.

It is therefore possible to carry out imaging through silicon with such cameras, and suitable lighting. However, their sensitivity in the case of wavelengths greater than 1 μm is mediocre and, unless particular care is taken, the measurements are made impossible by the reflectivity of the surfaces of the object 20.

The imaging device according to the invention comprises a first lighting path 23 intended to produce lighting in reflection of the bright field type. This lighting produces an illuminating beam 25 which is incident on the object 20 along an axis of illumination substantially parallel to the optical axis 49 of the imaging system. The light reflected or diffused on all the surfaces substantially perpendicular to the optical axis 49 contributes to the image in the camera 21.

The first lighting path 23 comprises a light source 24.

In the embodiment shown, this light source 24 comprises a halogen lamp connected to the optical system by an optical fibre bundle.

This light source 24 emits light in visible and near-infrared wavelengths.

The first lighting path 23 also comprises a spectral filter 26 inserted into the illuminating beam 25. The function of this spectral filter is to limit the spectrum of the illuminating beam 25 incident on the object 20 so that it essentially comprises only wavelengths which can penetrate or be transmitted into the object 20 (i.e. for which the object 20 is substantially transparent). In the present case, with an object 20 made of silicon, these are wavelengths of the order of 1 μm or more.

The spectral filter 26 thus makes it possible to minimize the reflections on the outer surface of the object 20 due to the wavelengths of the source 24 which cannot penetrate into the object 20 and which would therefore, without the filter 26, essentially be reflected by this surface.

Eliminating or at least strongly attenuating these reflections which would otherwise saturate the image in the camera 21 makes it possible to obtain an image of the structures (such as vias 3) situated below the surface of the object 20 with sufficient quality to be able to locate them.

Advantageously, the spectral filter 26 is constituted by a thin plate of the same material as the object 20, i.e., in the embodiment shown, silicon.

Thus, it can be produced at relatively low cost, whilst having spectral characteristics that are perfectly suited to the material of the object 20 since the wavelengths transmitted through the filter 26 are also those which are best transmitted through the surface of the object 20.

The first lighting path 23 also comprises a second light source 60 which makes it possible to generate an illuminating beam 25 with wavelengths for which the reflectivity of the surface of the object 20 is high (here the visible wavelengths), without passing through the spectral filter 26. In the embodiment shown, this second light source comprises a light-emitting diode. The light source 24 and the second light source 60 are electrically switched.

The imaging device according to the invention comprises a second lighting path 27 intended to produce lighting in reflection of the dark field type. This lighting produces an illuminating beam 30 which is incident on the object 20 along an axis of illumination which forms, with the optical axis 49 of the imaging system, an angle greater than the angle 35 defining the numerical aperture of the imaging system (i.e. the angle 35 between the optical axis 49 of the imaging system and the ray furthest from the optical axis 49 which enters the distal optic 36). In this configuration, only the light diffused (on the surface or in the object 20) in the direction of the optical imaging system contributes to the image in the camera 21.

In the embodiment of FIG. 1, the angle between the axis of the dark field illuminating beam 30 and the optical axis 49 of the imaging system is of the order of 60 degrees, which makes it possible to cover angles of approximately 50 degrees to 70 degrees.

The second lighting path 27 comprises a light source 28.

In the embodiment shown, this light source 28 comprises a halogen lamp connected to the optical system by an optical fibre bundle. This light source 28 emits light in visible and near-infrared wavelengths.

The second lighting path 27 also comprises a spectral filter 29 inserted into the illuminating beam 30. The function of this spectral filter is to limit the spectrum of the illuminating beam 30 incident on the object 20 so that it essentially comprises only wavelengths which can penetrate or be transmitted into the object 20 (i.e. for which the object 20 is substantially transparent). In the present case with an object 20 made of silicon, these are wavelengths of the order of 1 μm or more.

The spectral filter 29 thus makes it possible to minimize the reflections on the outer surface of the object 20 due to the wavelengths from the source 28 which cannot penetrate into the object 20 and which would therefore, without the filter 29, essentially be reflected by this surface.

Eliminating or at least strongly attenuating these reflections which would otherwise saturate the image in the camera 21 makes it possible to obtain an image of the structures (such as vias 3) situated below the surface of the object 20 with a sufficient quality to be able to locate them.

Advantageously, the spectral filter 29 is constituted by a thin plate of the same material as the object 20, i.e., in the embodiment shown, silicon.

Thus, it can be produced at relatively low cost, whilst having spectral characteristics that are perfectly suited to the material of the object 20 since the wavelengths transmitted through the filter 29 are also those which are best transmitted through the surface of the object 20.

The imaging device according to the invention comprises a third lighting path 31 intended to produce lighting in transmission. This lighting produces an illuminating beam 33 which is incident on the object 20 at its surface opposite the imaging system. The light transmitted through the object 20 contributes to the image in the camera 21, and thus makes it possible to visualize structures 2 of the object 20 which can be seen in transparency.

The third lighting path 23 comprises a light source 32.

In the embodiment shown, this light source 32 comprises a halogen lamp connected to the optical system by an optical fibre bundle. This light source 32 emits in particular light in near-infrared wavelengths, capable of passing through the object 20.

There is no problem with stray reflectivity in this lighting configuration since the reflections on the surfaces of the object 20 cannot be captured by the imaging means.

The system is designed so that the first, second and third lighting paths can be used simultaneously, or separately, in order to obtain images making it possible to locate structures in a wide variety of situations.

The light sources 24, 28 and 32 are adjustable in intensity.

The spectral filters 26, 29 can be easily changed in order to be suited to the materials of the object 20.

The dark field lighting of the second lighting path 27 makes it possible in certain cases to better locate structures 3, in particular in the case where they would be difficult to distinguish from the light background generated by the first lighting path 23.

It should be noted that, insofar as the system according to the invention is intended to carry out measurements on complex structures in a production environment, the possibility of producing complex lightings that are best suited to needs, in an automated manner or at least with minimum handling, is crucial.

Moreover, the utilization of the three lighting paths is not necessarily provided in all the configurations.

Measurement System

As explained previously, the measurement system comprises the imaging device and point optical distance or thickness measuring sensors 45, 46, 47.

These sensors are interfaced with the optical imaging means 34 so that the imaging device makes it possible to accurately position the measurement points on the object 20.

The point optical distance or thickness measuring sensors 4 as utilized in the embodiment of FIG. 1 will now be described.

The system according to the invention comprises a sensor 46 which operates according to a principle of time-domain low-coherence interferometry. This technique is also called "Time-Domain Optical Coherence Tomography" or TD-OCT.

Figure 3:
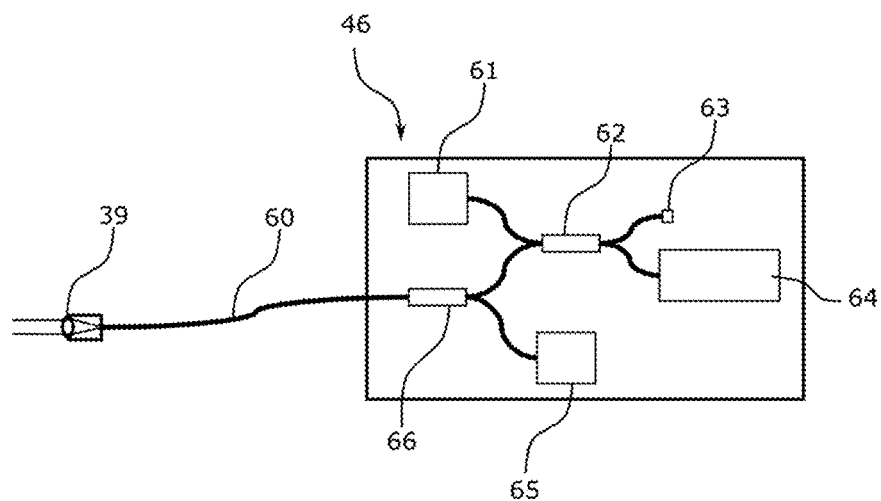
FIG. 3 shows a schematic diagram of a measuring sensor based on time-domain low-coherence interferometry.

FIG. 3 shows a schematic diagram of such a TD-OCT sensor 46, based on a fibre-optic interferometry architecture.

The TD-OCT sensor 46 comprises a light source 61 (such as a fibre-coupled superluminescent diode) which emits a polychromatic light in the near-infrared (for example around 1310 nm), so as to be able to penetrate the layers of the object 20.

The light from the source is split into two components by a fibre coupler 62. These two components are reflected by a delay line 64 and an internal reference 63 respectively, so as to introduce an optical delay between them. The reflections are recombined by the coupler 62, and directed towards a measurement collimator 39 and the object to be measured 20 through the coupler 66 and an optical fibre 60. An additional reflection is generated at the level of the measurement collimator 39, on a reference surface.

The light reflected by a measurement object 20 and collected on returning, by the measurement collimator 39, as well as the reflection on the reference surface in the collimator 39 are directed through the coupler 66 towards a detector 65.

Temporal scanning is carried out by the delay line 64. Each time the optical delay between the reference in the collimator 39 and a reflection on an interface of the object 20 is reproduced between the internal reference 63 and the delay line 64, an interference peak is obtained on the signal of the detector 65.

A signal is thus obtained, in which the position of the interference peaks as a function of the delay introduced into the delay line is directly representative of the succession or position of the interfaces of the object 20, on which the reflections took place.

It is thus possible to image structures of complex layers, for example along the measurement axis 10 of FIG. 2, and to obtain the succession of all the layers or of all the interfaces.

Advantageously, the measurement beam originating from the measurement collimator 39 is inserted into the optical imaging means 34, through the distal objective 36 of which in particular it passes. Thus, it is possible to carry out measurements whilst observing the object with the camera 21.

The TD-OCT sensor 46 comprises a second measurement path, with a collimation optic 40, which makes it possible to also carry out measurements via the surface opposite the object 20 relative to the imaging system.

This makes it possible to measure, for example, successions of layers of the object 20 on either side of an opaque structure 2, for example along the measurement axis 6.

Insofar as the TD-OCT sensor 46 provides absolute optical distance measurements relative to the reference in the collimators 39 or 40, this configuration, termed "caliper" measurement, also makes it possible to carry out thickness measurements on opaque structures 2, with suitable calibration of the two measurement paths 39, 40.

A drawback of the TD-OCT sensor 46 is that it does not make it possible to distinguish interfaces separated by less than a few micrometres. This limitation is due to the fact that the width of the interference peaks is an inverse function of the spectral width of the source 61, and the spectral width of the sources that are commercially available at reasonable cost is limited.

Advantageously, the system according to the invention also comprises a sensor 45 which operates according to a principle of frequency- or spectral-domain low-coherence interferometry. This technique is also called "Frequency Domain Optical Coherence Tomography", or FD-OCT.

The FD-OCT sensor 45 comprises a light source which emits a polychromatic light in the near-infrared, so as to be able to penetrate the layers of the object 20. Alternatively, it can utilize a wavelength-tunable source, the wavelength of which is varied over time so as to scan the useful spectrum.

The measurement beam of the FD-OCT sensor 45 is inserted, by means of a collimator 38, into the optical imaging means 34, through the distal objective 36 of which in particular it passes. Thus, it is possible to carry out measurements whilst observing the object with the camera 21.

The light reflected by the object 20 is analyzed in the FD-OCT sensor 45 by an optical spectrometer.

A spectrum is thus obtained, the ripples of which are representative of the thicknesses of the layers passed through by the measurement beam of the FD-OCT sensor 45. These ripples are due to the constructive or destructive interferences that appear at the different wavelengths, as a function of the optical distances between the reflections.

This method has the advantage of making it possible to measure small thicknesses, up to one micrometre or less depending on the spectral width of the source.

Its main drawback is that the spatial succession of the layers of the object 20 is not retained in the measurements: thickness measurements are obtained, the order or the sequence of which cannot be determined, which makes interpretation of the measurements difficult for a complex object 20.

Moreover, the maximum thickness that can be measured with an FD-OCT sensor depends on the resolution of the spectrometer, and therefore on the number of individual detectors that it comprises. This number of detectors is limited in existing spectrometers which use near-infrared sensors in InGaAs technology or multi-quantum wells. It follows that the maximum thickness that can be measured with an FD-OCT sensor is more limited than with the TD-OCT technique in which it is determined by the maximum delay which can be introduced by the delay line 64.

According to an advantageous aspect of the invention which distinguishes it from the devices of the prior art, the TD-OCT 46 and FD-OCT 45 sensors are used in a combined manner. This makes it possible, for example, to carry out measurements of the type of that of the measurement axis 8 of FIG. 2.

In this example, a transparent layer 4 of a thickness of the order of one micrometre is deposited on the component surface.

The TD-OCT sensor 46 provides the succession of the layers 10, but the deposit 4 is too thin for its thickness to be measured: It appears in the form of a single peak in the measurement signal of the TD-OCT sensor 46.

Advantageously, the complementary measurement carried out by the FD-OCT sensor 45 makes it possible to measure this thickness. Thus, by combining the measurements of the TD-OCT 46 and FD-OCT 45 sensors, a representation of the layers along the measurement axis 8 is obtained, which could not be achieved with only one of the two sensors.

The system according to the invention also comprises a distance sensor of the chromatic confocal type 47.

The chromatic confocal sensor 47 is utilized with a chromatic optic constituted by a dispersive element 41 and a collimator 42. These elements are designed so that the different wavelengths of the light originating from the chromatic confocal sensor 47 which passes through them are focussed at different distances at the level of the object 20. The reflections on the object 20 are collected by these chromatic optics 41, 42, and transmitted to a spectrometer in the chromatic confocal sensor 47. Analysis of the maximum values of the spectrum makes it possible to measure the position of the interfaces of the object 20 at the origin of these reflections.

The collimator 42 is mounted on the revolving nosepiece 37. The dispersive element 41 is integrated in the optical system by means of a mobile carriage 44 which moves a reflecting mirror 43. The measurement with the chromatic confocal sensor 47 cannot be carried out at the same time as the other measurements, but the elements are adjusted so that the optical axis of the chromatic optics 41, 42 coincides with the optical axis 49 of the imaging system, in order to be able to carry out measurements with the chromatic confocal sensor 47 in positions precisely located beforehand with the imaging system.

The chromatic confocal sensor 47 has the advantage of making it possible to measure absolute distances at a high rate, which cannot be achieved with the FD-OCT sensor 45 or with the TD-OCT sensor 46.

Thus, the three types of sensors utilized in the invention (TD-OCT 46, FD-OCT 45 and chromatic confocal 47) are highly complementary and make it possible to carry out measurements according to a large number of configurations on the object 20.

The whole of the system is controlled by means of a computer 48 and operating software, which on the one hand allow the best adjustment of the lighting paths in bright field 23, in dark field 27 and in transmission 31, and on the other hand make it possible to carry out measurements by optimally combining the TD-OCT 46, FD-OCT 45 and chromatic confocal 47 sensors.

Thus, complex measurement protocols can be carried out in semi-automated manner, on the basis of pre-programmed "recipes", with minimum handling on the part of the operator.

The measurements can also be automated, by utilizing a priori knowledge of the object 20, and/or image analysis techniques.

According to embodiment variants, the dark field lighting can be produced in the form of annular lighting.

According to embodiment variants, the spectral filters 26, 29 of the first and second lighting paths can be produced in any other manner making it possible to obtain suitable spectral characteristics. They can comprise in particular:
a superimposition of layers of dielectric materials in order to produce an interference filter,
a material different from those of the object 20 but having suitable spectral characteristics.

According to embodiment variants:
The spectral filter 26 of the first lighting path 23 can be mounted on a removable support which makes it possible to withdraw it from the illuminating beam 25. Similarly, the spectral filter 29 of the second lighting path 27 can be mounted on a removable support which makes it possible to withdraw it from the illuminating beam 30. This makes it possible to be able to image the surface of the object 20 under the best conditions, i.e. by utilizing the wavelengths of the light from the source 24 and/or light source 28 for which the reflectivity of the surface of the object 20 is high (here the visible wavelengths);
It is possible for the first lighting path 23 not to comprise a second light source 60;
The second lighting path 27 can also comprise a second light source which makes it possible to generate an illuminating beam 30 with wavelengths for which the reflectivity of the surface of the object 20 is high (here the visible wavelengths), without passing through the spectral filter 29;
Light sources 24, 60, 28, and/or 32 can be generated from one or more primary light sources shared between lighting paths 23, 27, 31, simultaneously or sequentially. This can in particular be achieved with suitable fibre bundles which convey the light from the primary source or sources towards the optical system;
The light sources 24, 60, 28, and/or 32 can comprise any suitable light source, such as for example discharge lamps or fibre-optic xenon lamps;
The light sources 24, 28, and/or 32 can comprise light sources with an emission spectrum limited to wavelengths capable of penetrating into the object 20, such as for example light-emitting diodes with an emission spectrum centred around 1050 nm. In this case, it is possible for the device according to the invention not to comprise a spectral filter 26, 29 in the first and/or the second lighting path 23, 27.

According to embodiment variants, configurations of sensors other than that shown in FIG. 1 can be envisaged, depending on the applications. These sensors can be based on other technologies, and/or measure dimensions other than distances and thicknesses.

The imaging device can also be completed by a full-field low-coherence interferometer, in order to carry out layout measurements on the object 20. This interferometer can be constituted at the level of the distal objective 36, so as to obtain, on the camera 21, interference fringes representative of the altitudes of the object 20. It can be constituted for example by inserting a semi-reflective plate between the distal objective 36 and the object 20, and a reference mirror between this semi-reflective plate and the distal objective 36. Layout measurements of the object 20 can thus be obtained by carrying out a controlled movement of this object 20 relative to the optical system so as to scan all the useful altitudes.

Figure 4:
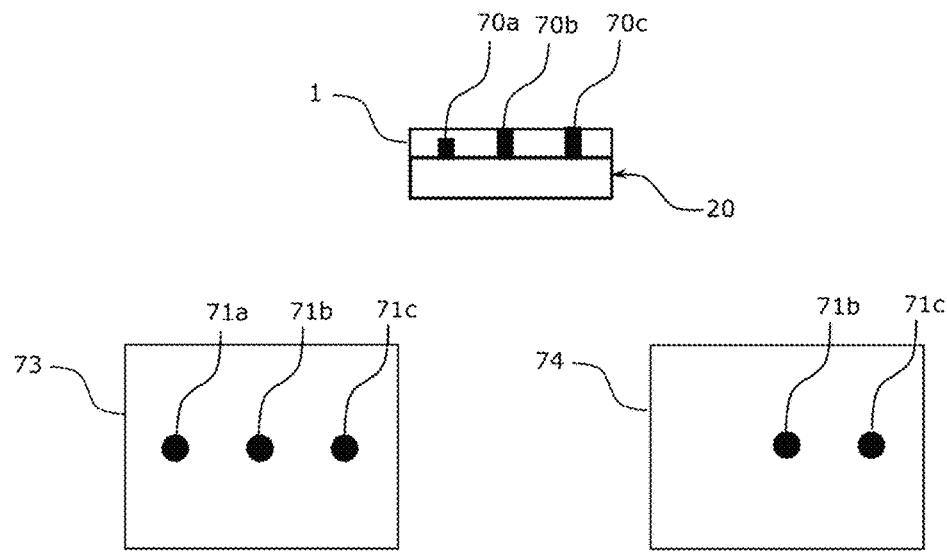
FIG. 4 shows another example of measurement problems.

FIG. 4 shows a measurement problem which is also solved by a measurement method utilizing an imaging device according to the invention.

The measurement object 20 shown in FIG. 4 comprises a silicon wafer 1, in which metallized vias 70*a*, 70*b*, 70*c* have been etched.

These vias (or "Through Silicon Vias", TSVs) correspond to hollow structures, such as trenches or holes, with a width of a few micrometres to several tens of micrometres. The structures are then filled with metal.

They are for example intended to produce interconnections between components or metal tracks and other components added in a subsequent step of the process to the outer surface of the wafer 1.

In order to be able to produce these interconnections, it is necessary to thin the wafer 1 in order to make the vias 70*a*, 70*b*, 70*c* apparent on its outer surface. This thinning operation is usually achieved by polishing the outer surface of the wafer 1.

It is important to be able to control whether all the vias have indeed been "revealed" on completion of the polishing, i.e. if they are all apparent on the outer surface. This makes it possible to optimize the polishing thickness, and to detect any defects linked to defects in the homogeneity of the polishing and/or defects in the structure of the vias.

This control must preferably be able to be carried out rapidly during polishing.

A method for controllably revealing vias is therefore proposed, which utilizes the imaging device according to the invention, and which has the advantage of being based only on the processing of images, without requiring the use of complementary dimensional measurement systems.

It thus makes it possible to carry out these measurements rapidly, and optionally with a simplified system.

A first image 73 of the object 20 is acquired by means of the camera 21, by illuminating this object with an illuminating beam the spectral content of which essentially comprises only wavelengths which can penetrate or be transmitted into this object 20 (i.e. for which the object 20 is substantially transparent).

This first image 73 can for example be obtained by using the first lighting path 23 intended to produce reflection lighting of the bright field type, with the light source 24 filtered by the spectral filter 26. It can also be obtained by using the second lighting path 27 intended to produce reflection lighting of the dark field type, with the light source 28 filtered by the spectral filter 29. Of course, it is also possible to utilize, without filters, light sources 24 or 28 the spectral content of which is limited to wavelengths which can penetrate or be transmitted into this object 20.

This first image 73 comprises images 71*a*, 71*b*, 71*c*, all the structures or vias 70*b*, 70*c* present at the surface of the wafer 1 (i.e. "revealed") as well as all the structures 70*a* still buried in proximity to this surface. Due to the choice of the wavelengths, this is an image in transparency in which the effect of the surface of the wafer 1 is minimized.

A second image 74 is also acquired by means of the camera 21, by illuminating this object with an illuminating beam the spectral content of which comprises wavelengths for which the reflectivity of the surface of the object 20 is high (here the visible wavelengths).

This second image 74 can for example be obtained by using the first lighting path 23 intended to produce reflection lighting of the bright field type, with the second unfiltered light source 60.

This second image 74 comprises only images 71*b*, 71*c* of the structures or vias 70*b*, 70*c* present at the surface of the wafer 1 (i.e. "revealed").

Due to the high reflectivity of the surface, the structures 70*a* which are still buried cannot be seen, even if they are in immediate proximity to this surface.

In the case where the object 20 comprises silicon, the first image is acquired with wavelengths in the near-infrared, greater than 1 micrometre, and the second image is acquired with wavelengths in the visible spectrum.

The method according to the invention then comprises a step of comparative analysis of the images in transparency 73 and of the surface 74, in order to identify structures 70*a* which are not revealed, i.e. which do not appear at the surface.

This comparative analysis can for example comprise steps of segmentation of the first and second images, and comparative analysis of the segmented zones.

This method for controllably revealing vias can of course be implemented with a complete measurement system as shown in FIG. 1.

Figure 5:
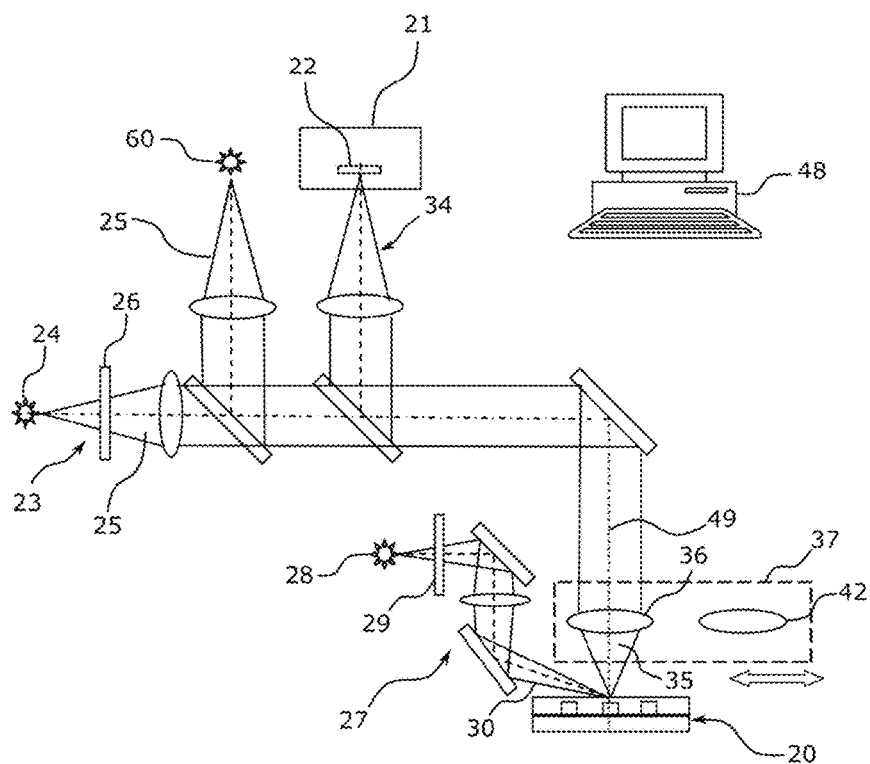
FIG. 5 shows another embodiment of an imaging system according to the invention.

It can also be implemented with an imaging device as shown in FIG. 5, when this device allows the acquisition of images:

by illuminating the object 20 with a first illuminating beam the spectral content of which is suited to the nature of the object so that the light of said beam is capable essentially of penetrating into said object, by illuminating the object 20 with a second illuminating beam the spectral content of which is suited to the nature of the object so that the light of said beam is essentially reflected by the surface of the object.

It should be noted that the imaging device shown in FIG. 5 is identical to the complete measurement system as shown in FIG. 1 as regards the common parts. Thus, the entire detailed description of these common parts with respect to FIG. 1 is also directly applicable to the device of FIG. 5.

It is also possible to implement the method for controllably revealing vias with a device conforming to that shown in FIG. 5, but which does not comprise a second lighting path 27 intended to produce reflection lighting of the dark field type.

Of course, the invention is not limited to the examples which have just been described, and numerous adjustments can be made to these examples without exceeding the scope of the invention.

The invention claimed is:

1. An imaging method for locating and controlling for the presence, at a surface of an object such as a wafer, of structures enclosed in said object such as vias, utilizing an imaging sensor, optical imaging means capable of producing on the imaging sensor an image of the object and of the structures in a field of view, and illuminating means for generating illuminating beams and illuminating the field of view in reflection, the illuminating beams being incident in the field of view along an axis of illumination substantially parallel to the optical axis of the optical imaging means, the method comprising the steps of:

acquiring a first image of the object comprising images of first structures present at the surface of the object as well as second structures buried in proximity to said surface so as to visualize said first and second structures, by illuminating the object with a first illuminating beam the spectral content of which is suited to the nature of the object so that the light of said first illuminating beam is configured to penetrate into the object;

acquiring a second image of the object comprising only images of said first structures present at the surface of the object so as to visualize said first structures by illuminating the object with a second illuminating beam the spectral content of which is suited to the nature of the object so that the light of said second illuminating beam is reflected by the surface of the object; and comparing said first and second images so as to locate and identify said second structures that appear in the first image but not in the second image.

2. An imaging device for locating and controlling for the presence, at a surface of an object such as a wafer, of structures such as vias enclosed in said object, the device comprising:

an imaging sensor;

optical imaging means arranged for producing on said imaging sensor an image of the object comprising images of the structures so as to visualize the structures in a field of view;

illuminating means for generating illuminating beams and lighting said field of view in reflection, said illuminating beams being incident in the field of view along an axis of illumination substantially parallel to the axis of the optical imaging means;

the illuminating means being capable of:

generating a first illuminating beam, the spectral content of which is suited to the nature of the object, so that the light of said first illuminating beam is configured to penetrate into said object; and generating a second illuminating beam, the spectral content of which is suited to the nature of the object, so that the light of said second illuminating beam is reflected by the surface of the object.

3. The device of claim 2, in which the illuminating means comprise a spectral filter capable of limiting the spectrum of the first illuminating beam to wavelengths which are capable essentially of penetrating into the object.

4. The device of claim 3, in which the spectral filter comprises a plate made of a material identical or similar to a material of the object.

5. The device of claim 3, in which the spectral filter comprises a silicon plate.

6. The device of claim 3, in which the illuminating means also comprise:

a light source capable of emitting light with a spectrum comprising first wavelengths capable essentially of being reflected by the surface of the object and second wavelengths capable essentially of penetrating into the object, and switching means for inserting the spectral filter into, or withdrawing it from, the first illuminating beam.

7. The device of claim 2, in which the illuminating means comprise a light source capable of emitting a light the spectrum of which is limited to wavelengths capable of penetrating into the object.

8. The device of claim 7, in which the illuminating means also comprise a second light source capable of emitting a light the spectrum of which is limited to wavelengths capable of being reflected by the surface of the object.

9. The device of claim 1, which comprises an illuminating beam incident in the field of view along an axis of illumination substantially parallel to the optical axis of the imaging system.

10. The device of claim 1, which comprises an illuminating beam incident in the field of view along an axis of illumination forming, with the optical axis of the imaging system, an angle greater than the angle defining the numerical aperture of said imaging system.

11. The device of claim 1, which also comprises a light source in transmission arranged so as to illuminate the field of view in transmission, through the object.

12. The device of claim 1, in which the imaging sensor comprises a CCD- or CMOS-type sensor on a silicon substrate.

* * * * *